United States Patent [19]

Cordes et al.

[11] Patent Number: 5,753,256
[45] Date of Patent: May 19, 1998

[54] PLASTER FOR THE TREATMENT OF NAIL MYCOSES

[75] Inventors: Günter Cordes, Leichlingen; Ulrike Vollmer, Mönchengladbach, both of Germany

[73] Assignee: Labtec Gesellschaft fur Biotechnologische Forschung und Entwicklung mbH, Langenfeld, Germany

[21] Appl. No.: 637,791

[22] PCT Filed: Nov. 4, 1994

[86] PCT No.: PCT/EP94/03624

§ 371 Date: May 6, 1996

§ 102(e) Date: May 6, 1996

[87] PCT Pub. No.: WO95/12393

PCT Pub. Date: May 11, 1995

[30] Foreign Application Priority Data

Nov. 6, 1993 [DE] Germany ............... 43 37 945.1

[51] Int. Cl.⁶ ............................................ A61K 9/70
[52] U.S. Cl. ............ 424/443; 424/449; 514/223.8; 514/397; 514/481; 514/599; 514/652

[58] Field of Search ................ 424/443, 449; 514/223.8, 397, 599, 481, 657

[56] References Cited

U.S. PATENT DOCUMENTS

| | | | |
|---|---|---|---|
| 5,176,916 | 1/1993 | Yamanaka et al. | 424/448 |
| 5,264,206 | 11/1993 | Bohn et al. | 424/61 |
| 5,415,903 | 5/1995 | Hoffman et al. | 428/15 |
| 5,446,070 | 8/1995 | Mantelle | 514/722.6 |
| 5,464,610 | 11/1995 | Hayes, Jr. et al. | 424/61 |

FOREIGN PATENT DOCUMENTS

| | | |
|---|---|---|
| 4140888 | 6/1993 | Germany. |
| 1011115 | 4/1983 | U.S.S.R. . |
| 9311734 | 11/1993 | WIPO . |

*Primary Examiner*—Kevin E. Weddington
*Attorney, Agent, or Firm*—Kane, Dalsimer, Sullivan, Kurucz, Levy, Eisele and Richard

[57] ABSTRACT

The invention relates to a plaster for the treatment of nail mycoses, which is characterized by an antimycotically active substance, clotrimazole and bifonazole being excluded.

9 Claims, No Drawings

PLASTER FOR THE TREATMENT OF NAIL MYCOSES

The invention relates to a plaster for the treatment of nail mycoses.

Fungal diseases of the nails are a widespread phenomenon. Indications are found in the specialist medical literature that 8% of the population suffer from them. The fact that there is a relatively high risk of infection in a damp environment (for example in swimming baths or when wearing shoes or protective gloves) plays a part here. This is a disease which only clears poorly and needs treatment.

As methods of treatment, there is the possibility of detaching the affected nail after appropriate pretreatment, which, however, is refused by many affected persons because of the unpleasantness associated with it. Additionally, modern antimycotics have recently been developed which act on fungal diseases of the nail even after oral administration. However, the treatment must be carried out over a long period of a few months, side effects occurring during the oral treatment since the whole body comes into contact with the medicament. The result is that the patient terminates the therapy and thus the fungal disorder does not clear.

Solutions and even nail varnish have been developed which contain antifungal active compounds to be released only locally at the sites of the disorder, and which thus do not have the side effects of oral therapy. However, the fungal population is in the nail bed under the nail plate (cf. Charlet, Kosmetik für Apotheker, Wissenschaftliche Verlagsgesellschaft mbH, Stuttgart 1989), which the active compound must first get through. Solutions are washed off too rapidly, for example when washing or showering, and even a nail varnish cannot absorb sufficient active compound and permeation promoters or enhancers, i.e. substances which channel the active compound through the nail to the site of the fungal disorder. In this respect, an effective local treatment has been a problem until now.

According to the invention, a plaster for the treatment of nail mycoses is now proposed which is characterized by an antimycotically active substance (active compound), clotrimazole and bifonazole being excluded.

Preferred embodiments are clear from the sub-claims.

What is concerned here is a plaster containing an antimycotic, which is stuck onto the affected nail. The antifungal active compound can be embedded for this purpose in a polymer matrix which consists, for example, of an acrylate copolymer. Substances can furthermore be embedded in the matrix which can bring the active compound out of the matrix and/or through the nail, i.e. so-called permeation promoters or enhancers which especially affect protein-rich barriers of the nails, for example the keratin.

Moreover, additives can be added, for example Aerosil or crosslinkers customary for an acrylate copolymer, which regulate the adhesive properties. The system is thus single-layered, which simplifies the production process. The matrix can be provided with a covering film in order that no adverse effects takes place when wearing it as a result of the adhesive properties of the matrix, and the matrix with the substances contained in it is not removed when washing.

A further advantage of the plaster according to the invention is to be seen in the possibility of embedding sufficiently large amounts of active compound in the matrix in order to maintain the flow of the active compound through the nail for a long time, which is a property which is important for fungal control.

A plaster according to the invention can contain 1.1 to 1.7 mg of active compound per $cm^2$, so as a rule a dose of 3 to 6 mg is applied to the nail, depending on individual size. The plaster according to the invention can in this case be designed such that the plaster can remain on the nail for several days, which favours patient compliance and lowers the treatment costs.

In the production of a plaster according to the invention, particular attention is paid to the selection of the polymers, the permeation promoters, the adhesive properties and the covering film. The polymers should absorb an adequate amount of the active compound in dissolved form and the permeation promoters must improve the permeation of the active compound through the nail. The active compound-containing adhesive matrix has, according to the invention, a strong adhesive force to the nail, but can be peeled off after wearing. According to the invention, a cosmetically innocuous covering film is provided which has sufficient flexibility in order to be well fitted to the nail even if the nail has an uneven surface. The covering film consists preferably of soft PVC, which in particular contains a skin-coloured pigment. Commercially available cosmetic nail varnish can optionally be applied to this film without the therapy of the nail mycosis being affected thereby.

The invention is illustrated in greater detail below by means of an example.

EXAMPLE 1

For the production of 1800 $cm^2$ plaster surface area, 2.5 g of miconazole are dissolved as far as possible in ethyl acetate with stirring. 0.9 g of dimethyl sulphoxide is added, the mixture is stirred again, then 60 g of a 49.1% solution of Durotak 901–1052 are added and the mixture is stirred until it is homogeneous. It is then spread onto a polyester film (75 μm thickness) which is siliconized on both sides, such that the wet film thickness is 500 μm. After drying over the course of 2 h in a drying oven at 60° C. and storage at 25° C. over the course of 12 h, lamination takes place with a polyolefin film of a thickness of 50 μm (Cotran 9722). Then, using a punch, plasters 4.5 $cm^2$ in size are punched out. When applying, the patient cuts the plaster to the particular size of the nail.

We claim:

1. A plaster for sticking onto the human nail, which comprises;

a flexible covering film;

a layer of an acrylate polymer matrix inseparably linked with the covering film and containing an effective amount of an antimycotically active compound and a promoter for promoting the permeation of the active compound through the nail;

said polymer matrix being the product of free-radical polymerization of at least one compound selected from the group consisting of 2-ethylhexyl acrylate, butyl acrylate, methyl acrylate, acrylic acid, vinyl acetate, hydroxyethyl acrylate and glycidyl methacrylate;

said active compound being selected from the group consisting of miconazole, econazole, isoconazole, tioconazole, terconazole, oxiconazole, ketoconazole, itraconazole, tolciclate, sulbentine, haloprogin, griseofulvin, cyclopirox, terbinafin, and salts thereof.

2. The plaster of claim 1 wherein the free-radical polymerization is of 50 to 80% of 2-ethylhexyl acrylate, 5 to 20% of butyl acrylate, 20 to 40% of methyl acrylate, 2 to 8% of acrylic acid, 2 to 30 of vinyl acetate, 0.5 to 3% of hydroxyethyl acrylate and 0.02 to 0.1% of glycidyl methacrylate, in each case on a weight basis and relative to the polymer matrix without active compound and permeation promoter.

3. Plaster according to claim 2, wherein a polymer matrix based on acrylate for a plaster of 3 to 6 cm² surface area, obtainable by polymerization of 70 to 80% of 2-ethylhexyl acrylate, 12 to 18% of butyl acrylate, 2.8 to 6.8% of acrylic acid and 3 to 7% of vinyl acetate.

4. Plaster according to claim 2, wherein a polymer matrix based on acrylate for a plaster of 3 to 6 cm² surface area, obtainable by polymerization of 72 to 83% of 2-ethylhexyl acrylate, 1.5 to 3.3% of acrylic acid, 15 to 25% of vinyl acetate and optionally 0.1 to 0.8% of aluminum acetylacetonate and/or 0.1 to 0.35% of titanium acetylacetonate.

5. Plaster according to one of claim 1 wherein the permeation promoters used are sulphoxides.

6. Plasters according to one of claims 1–5, wherein that the permeation promoters used are dimethyl sulphoxide in a concentration in the matrix of 1 to 6% or lactic acid in a concentration of 1 to 6% (in each case concentration in the matrix).

7. The plaster according to claim 5 wherein at least one permeation enhancer is used selected from the group consisting of dimethylsulfoxide, decylmethylsulphoxide, pyrrolidones, dimethylformamide, dimethylacetamide, sodium dodecylsulphate, propylene glycol and salicylic acid.

8. The plaster according to claim 1 which further comprises a protective layer over the matrix.

9. A plaster for sticking onto the human nail, which comprises;

a flexible covering film;

a layer of an acrylate polymer matrix inseparably linked with the covering film and containing an effective amount of an antimycotically active compound and promoter for promoting the permeation of the active compound through the nail;

said polymer matrix being the product of free-radical polymerization of at least one compound selected from the group consisting of 2-ethylhexyl acrylate, butyl acrylate, methyl acrylate, acrylic acid, vinyl acetate, hydroxyethyl acrylate and glycidyl methacrylate; provided that when the antimycotically active compound is selected from the group consisting of clotinazole and bifonzole, there is also present an effective amount of an active compound selected from the group consisting of miconazole, econazole, isoconazole, tioconazole, terconazole, oxiconazole, ketoconazole, itraconazole, tolciclate, sulbentine, haloprogin, griseofulvin, cyclopirox, terbinafin and salts thereof.

* * * * *